United States Patent
Cai et al.

(10) Patent No.: US 11,629,338 B2
(45) Date of Patent: Apr. 18, 2023

(54) METHOD FOR ACCLIMATING AND SUSPENDING VERO AND SECOND ORDER PRODUCTION PROCESS FOR VIRUS

(71) Applicant: Jianshun Biosciences Co., Ltd., Gansu (CN)

(72) Inventors: Shijun Cai, Gansu (CN); Ruijuan Hou, Gansu (CN)

(73) Assignee: JIANSHUN BIOSCIENCES CO., LTD., Lanzhou (CN)

( * ) Notice: Subject to any disclaimer, the term of this patent is extended or adjusted under 35 U.S.C. 154(b) by 428 days.

(21) Appl. No.: 16/761,049

(22) PCT Filed: Nov. 9, 2017

(86) PCT No.: PCT/CN2017/110128
§ 371 (c)(1),
(2) Date: May 1, 2020

(87) PCT Pub. No.: WO2019/090565
PCT Pub. Date: May 16, 2019

(65) Prior Publication Data
US 2021/0180027 A1    Jun. 17, 2021

(51) Int. Cl.
| | |
|---|---|
| *C12N 5/071* | (2010.01) |
| *A01N 1/02* | (2006.01) |
| *C12N 7/00* | (2006.01) |
| *A61K 39/215* | (2006.01) |
| *A61K 39/00* | (2006.01) |

(52) U.S. Cl.
CPC ......... *C12N 5/0686* (2013.01); *A01N 1/0284* (2013.01); *A61K 39/215* (2013.01); *C12N 7/00* (2013.01); *A61K 2039/525* (2013.01); *C12N 2770/18034* (2013.01); *C12N 2770/18052* (2013.01)

(58) Field of Classification Search
None
See application file for complete search history.

(56) References Cited

U.S. PATENT DOCUMENTS

| | | | |
|---|---|---|---|
| 2009/0203112 A1* | 8/2009 | Daelli | C12N 7/00 435/235.1 |
| 2021/0180027 A1* | 6/2021 | Cai | A61K 39/215 |

FOREIGN PATENT DOCUMENTS

| | | |
|---|---|---|
| CN | 103550772 A | 2/2014 |
| CN | 104436184 A | 3/2015 |
| CN | 104862270 A | 8/2015 |
| CN | 106047821 A | 10/2016 |
| WO | 02/24876 A2 | 3/2002 |

OTHER PUBLICATIONS

Toriniwa et al. (Vaccine. 2008; 3680-3689).*
(Continued)

*Primary Examiner* — Shanon A. Foley
(74) *Attorney, Agent, or Firm* — Morgan, Lewis & Bockius LLP

(57) ABSTRACT

Disclosed is a second-order culture method for producing a suspended Vero cell vaccine, wherein same comprises the following steps: suspension culture growth of Vero cells, inoculation of a virus, dilution or addition of a production medium, secondary growth of cells, and optionally harvesting and purifying the virus fluid to produce the vaccine.

14 Claims, 1 Drawing Sheet

Suspension Vero cell growth 20 ×

Suspension Vero cell growth 40 ×

Suspension Vero cell lesion 20 ×

Suspension Vero cell lesion 40 ×

(56) References Cited

OTHER PUBLICATIONS

Paillet et al. (Vaccine. 2009; 27: 6464-6467).*
Rourou et al. (Vaccine. 2019; 37: 6987-6995).*
Shen et al. (Vaccine. 2019; 37: 6996-7002).*
Extended European Search Report issued in counterpart European Patent Application No. 17931137.8 dated Jun. 29, 2021.
International Search Report issued in corresponding International Patent Application No. PCT/CN2017/110128 dated Jul. 18, 2018.

* cited by examiner

Suspension Vero cell growth 20 ×    Suspension Vero cell growth 40 ×

Suspension Vero cell lesion 20 ×    Suspension Vero cell lesion 40 ×

METHOD FOR ACCLIMATING AND SUSPENDING VERO AND SECOND ORDER PRODUCTION PROCESS FOR VIRUS

TECHNICAL FIELD

The present invention relates to the fields of methods for acclimating and suspending Vero cells, and the production of suspension Vero cells-associated vaccines. The methods for acclimating and suspending Vero cells and a second-order (two-stage) virus production process of the present invention may exist simultaneously or independently in the technical solutions. Specifically, present invention relates to a process technology for cultivating suspension Vero cells in a bioreactor bigger than 30 L, and cultivating suspension Vero cells in a second-order cultivation method to produce vaccines.

BACKGROUND ART

The large-scale cultivation technology of mammalian cells is one of the general downstream technologies of biopharmaceutical companies, which plays an extremely important role in this industry. The key point of this technology is to achieve a large-scale serum-free cultivation of suspension mammalian cells, thereby increasing productivity, reducing costs, and easy to scale up. The usual practice in adherent cell cultivation is to add a certain amount of serum to the culture medium to make the cells grow in an adherence manner, however the chemical compositions of serum are uncertain, and the quality thereof is instable, and there are batch-to-batch differences. Accordingly, it is difficult to control the quality of the biological products produced with such cells, and it is difficult to obtain an approval from the Food and Drug Administration. Compared with the common adherent cultivation, serum-free suspension cultivation can grow more cells per unit volume and thus produce more biological products.

Vero cells, also known as *Cercopithecus aethiops* kidney cells (Verda Reno), are transformed cells obtained from normal adult *Cercopithecus aethiops* kidney cells in 1962. The cell is an adherence-dependent fibroblast and can support the proliferation of various viruses, including encephalitis type B virus, poliovirus, Vaccinum Rabiel and the like, which has been approved for the production of various human and veterinary viral vaccines.

The defects of the existing methods for acclimating and suspending Vero cells are: 1. some of them are incapable of achieving complete serum-free cultivation; 2. generally, a two-step process is involved, that is, firstly reducing to serum-free and then suspension cultivation, however since the medium employed for adherent cultivation is usually a basal medium plus serum, of which the nutritional ingredients is poor, and the surface area/volume ratio of adherent cultivation during acclimation is usually small, which limits the intake of nutrients, the entire acclimation process takes a long time; 3. acclimation after genetic modification, that is, by genetic modification, inserting gene fragments bad for adherence into adherent cell strains to change the original adherent cultivation means to make cells grow in a suspension manner, and then through continuous optimization and change of the culture medium to enable cells to grow at high density without serum. This method is easy to be accomplished, but the quality of the products obtained will be affected due to the inserted exogenous gene fragments. Therefore, there is a need to further study the methods of suspension acclimation and serum-free acclimation of Vero cells to overcome the above three defects.

With respect to virus inoculation process, the traditional production process of viral vaccines is that after the cells have grown to a certain density, the medium is changed and then viruses are inoculated, or the viruses are directly inoculated. Up to now, there is no report about the second-order culture method of suspension Vero cells.

SUMMARY OF THE INVENTION

A first aspect of the present invention relates to a second-order (two-stage) cultivation method for producing vaccines with suspension Vero cells, comprising the following steps:
1) cell growth: suspension Vero cells are grown in a growth medium to $2.0 \times 10^6$ cells/mL~$20.0 \times 10^6$ cells/mL;
2) inoculation: the inoculation amount is between $10^{-1}$~$10^{-5}$ multiplicities of infection (MOIs), or viruses are inoculated after step 3) according to this inoculation amount;
3) dilution/supplementation of a production medium: diluting 1 to 5 times with the production medium, and after dilution, the cell density reaches $1.0 \times 10^6$ cells/mL to $10.0 \times 10^6$ cells/mL;
4) secondary growth: secondary growth of cells;
5) optionally, the virus solution is harvested and purified for vaccine preparation.

In some embodiments, the growth of suspension Vero cells is a suspension cultivation tank cultivation with a cultivation working volume of 30 L and above.

In some embodiments, the cell density in step 1) is $5.0 \times 10^6$ cells/mL to $16.0 \times 10^6$ cells/mL, preferably, $6.0 \times 10^6$ cells/mL to $15.0 \times 10^6$ cells/mL, most preferably, $10.0 \times 10^6$ cells/mL.

In some embodiments, in step 2), the inoculation amount to the cells is between $10^{-1}$~$10^{-4}$ MOIs, more preferably, $10^{-1}$~$10^{-3}$ MOIs, most preferably, $10^{-2}$ MOIs.

In some embodiments, the production medium for suspension Vero cells in step 3) is diluted 1 to 4 times, more preferably, 1 to 3 times, and most preferably, 2 times.

In some embodiments, the cell density after inoculation in step 3) is $1.0 \times 10^6$ cells/mL to $10.0 \times 10^6$ cells/mL, preferably, $4.0 \times 10^6$ cells/mL to $10.0 \times 10^6$ cells/mL.

In some embodiments, the suspension Vero cells are suspension cells used for vaccine production, or suspension Vero cells acclimated from adherent Vero cells and capable of suspension growth and production, preferably, the suspension Vero cells are obtained from adherent Vero cells by low serum acclimation or serum-free acclimation. The term "serum-free acclimation" means that the acclimated Vero cells can grow and proliferate in a medium without serum, and/or, preferably, suspension Vero cells are obtained from adherent Vero cells by suspension acclimation.

In some embodiments, the virus is a virus that is sensitive to the corresponding suspension Vero cells and is capable of producing the corresponding vaccines. Preferably, the virus is selected from the group consisting of rabies vaccine (RV), porcine epidemic diarrhea vaccine (PEDV), Japanese encephalitis virus vaccine and Polio vaccine.

In some embodiments, the cell growth temperature is between 35° C. and 37° C., and the virus production temperature after inoculation is between 30° C. and 37° C.

In some embodiments, the cell growth seeding density is between $0.3 \times 10^6$ cells/mL to $1.0 \times 10^6$ cells/mL, and the growth reaches the highest cell density within 2 to 8 days.

In other words, a technical problem solved by the present invention is to overcome the defects of the prior art, and to provide a low-serum acclimation method, a serum-free acclimation method and a suspension acclimation method for adherent Vero cells, so that said cells grow in a stable growth state, have good dispersibility, and are suitable for large-scale cultivation and facilitate the replication and expression of the virus.

To this end, the present invention enables the original, adherently growing cell lines to grow in a low serum and/or serum-free culture medium in high-density suspension manner by changing the culture medium and the cultivation modes. In particular, low serum acclimation involves gradually reducing the serum concentration of the medium during the passages of the cells until the Vero cells are adapted to the cultivation conditions at a low serum concentration. The initial Vero cells in the best state and stably growing for low serum acclimatization may be Vero cells thawed and recovered from cryopreserved adherent Vero cells.

Subsequently, after Vero cells have fully adapted to adherent, low serum growth, the serum-free, chemically defined growth medium Celkey® CD Vero211 (JSB-DP211) is used for serum-free acclimation and suspension acclimation, until Vero cells are fully adapted to suspension cultivation. In addition, the suspended Vero cells can stably subculture and grow, the density of suspended Vero cells can reach $8.0 \times 10^6$ cells/mL~$20.0 \times 10^6$ cells/mL, and the viability is maintained above 95%.

The Vero cells in the present invention have the characteristics of the cell line identified as American Type Culture Collection (ATCC) accession No. CCL-81, and are commercially available. The suspension Vero cells in the present invention are suspension Vero cells adapted to serum-free suspension culture, and may be commercially available suspension Vero cells, or may be suspension Vero cells obtained by low serum acclimating, serum-free acclimating and/or suspension acclimating adherent Vero cells as described above. Celhappy® BD004 (JSB-DP049) medium is a commercial medium from Jianshun Bio., and Celkey® CD Vero211 (JSB-DP211) is a commercial medium from Jianshun Bio. Compared with the prior art, the present invention has the following advantages: the suspension Vero cells cultured with the method of the present invention have a stable growth state and a good dispersibility, and are fully adapted to suspension culture in a serum-free, chemically defined medium, and can be produced in a large-scale.

The invention also provides a second-order culture method for producing suspension Vero cell-associated vaccines, comprising the following steps:
1) cell growth: suspension Vero cells are grown in a growth medium to $2.0 \times 10^6$ cells/mL~$20.0 \times 10^6$ cells/mL;
2) inoculation: according to a production process, on day 2 or day 3 of cell growth, the cell density reaches $6.0 \times 10^6$ cells/mL~$10.0 \times 10^6$ cells/mL, and a $10^{-1}$~$10^{-5}$ MOIs inoculation amount is selected, or the inoculation is carried out after dilution in accordance with this inoculation amount;
3) dilution/supplementation of a virus production medium: diluting 1 to 5 times with the production medium. After dilution, the cell density reaches $1.0 \times 10^6$ cells/mL to $10.0 \times 10^6$ cells/mL;
4) secondary growth: secondary growth of cells;
5) optionally, the virus solution is harvested and purified for vaccine preparation.

In some embodiments, the expression of "the virus solution is harvested and purified for vaccine preparation" refers to harvesting and purifying the virus solution for vaccine preparation according to a production process, wherein the production process refers to a known production process used for producing a corresponding vaccine with Vero cells.

In some embodiments, the growth of Vero cells is a suspension cultivation tank cultivation with a cultivation working volume of 30 L and above, such as 35 L, 40 L, 50 L, 100 L, 150 L, 200 L, 300 L, 400 L, 500 L or larger.

In some embodiments, the growth medium of Vero cells is any medium suitable for the growth of Vero cells, preferably, the medium is Celkey® CD Vero211 (JSB-DP211) serum-free medium.

In some embodiments, the cell density in step 1) is $5.0 \times 10^6$ cells/mL to $16.0 \times 10^6$ cells/mL, preferably, $6.0 \times 10^6$ cells/mL to $15.0 \times 10^6$ cells/mL, most preferably, $10.0 \times 10^6$ cells/mL.

In some embodiments, the inoculation amount to the cells in step 2) is between $10^{-1}$~$10^{-4}$ MOIs, more preferably, $10^{-1}$~$10^{-3}$ MOIs, most preferably, $10^{-2}$ MOIs.

In some embodiments, the production medium for Vero cells in step 3) is diluted 1-4 times, more preferably, 1-3 times, and most preferably, 2 times.

In some embodiments, the cell density after inoculation in step 3) is $2 \times 10^6$ cells/mL to $7.0 \times 10^6$ cells/mL, preferably, $3.0 \times 10^6$ cells/mL to $5.0 \times 10^6$ cells/mL.

In some embodiments, the cell density after the secondary growth in step 4) is $2.0 \times 10^6$ cells/mL-$20.0 \times 10^6$ cells/mL, for example, $2.0 \times 10^6$ cells/mL, $3.0 \times 10^6$ cells/mL, $4.0 \times 10^6$ cells/mL, $5.0 \times 10^6$ cells/mL, $6.0 \times 10^6$ cells/mL, $7.0 \times 10^6$ cells/mL, $8.0 \times 10^6$ cells/mL, $9.0 \times 10^6$ cells/mL, $10.0 \times 10^6$ cells/mL, $11.0 \times 10^6$ cells/mL, $12.0 \times 10^6$ cells/mL, $13.0 \times 10^6$ cells/mL, $14.0 \times 10^6$ cells/mL, $15.0 \times 10^6$ cells/mL, $16.0 \times 10^6$ cells/mL, $17.0 \times 10^6$ cells/mL, $18.0 \times 10^6$ cells/mL, $19.0 \times 10^6$ cells/mL, $20.0 \times 10^6$ cells/mL.

In some embodiments, the Vero cells are suspension cells used for vaccine production, or suspension cells acclimated from adherent cells and capable of suspension growth and production.

In some embodiments, the virus is a virus that is sensitive to the corresponding suspension Vero cells and is capable of producing the corresponding vaccines. In some embodiments, the virus is selected from the group consisting of human rabies vaccine, Japanese encephalitis virus vaccine, polio vaccine and porcine epidemic diarrhea vaccine.

In some embodiments, the cell growth temperature is between 35° C. and 37° C., and the virus production temperature after inoculation is between 30° C. and 37° C.

In some embodiments, the cell growth seeding density ranges from $0.3 \times 10^6$ cells/mL to $1.0 \times 10^6$ cells/mL, for example, $0.3 \times 10^6$ cells/mL, $0.4 \times 10^6$ cells/mL, $0.5 \times 10^6$ cells/mL, $0.6 \times 10^6$ cells/mL, $0.7 \times 10^6$ cells/mL, $0.8 \times 10^6$ cells/mL, $0.9 \times 10^6$ cells/mL or $1.0 \times 10^6$ cells/mL, and the growth reaches the highest cell density within 3 to 8 days, such as 3 days, 4 days, 5 days, 6 days, 7 days or 8 days.

The innovation of the present invention is that before the cells grow to the stationary stage, the cell density reaches the highest level, then the original culture volume is diluted, and then the virus is inoculated. The diluted cells can grow from low density secondarily, and the virus also replicates simultaneously, eventually increasing virus production. The advantages of the second-order culture for the production of the Vero cell-associated vaccine of the present invention are: simple production process; no waste of culture medium; no medium exchange; the production medium and the growth medium can be the same medium or different media. The production medium and the growth medium are mixed according to a ratio, which can not only achieve the cell growth, but also achieve the virus replication and proliferation.

DETAILED DESCRIPTION OF THE INVENTION

Figure 1:
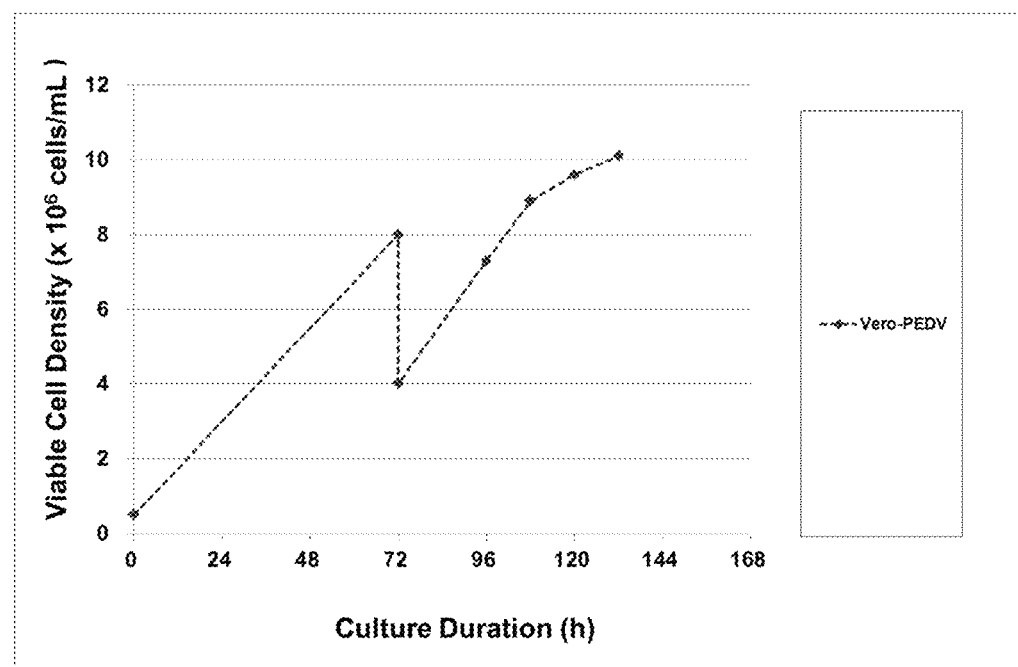
FIG. 1 shows that when the cell density of Vero cells reached to $8.0\times10^6$ cells/mL on day 3, the cell culture medium was doubled to the original working volume, and the cell density was diluted to $3.1\times10^6$ cells/mL, then the virus was inoculated, and the cells began to grow again. After 2 days, the cell density reached to $12.0\times10^6$ cells/mL.

In other words, the innovation of the present invention lies in: after acclimating adherent Vero cells by the low-serum acclimation method, the serum-free acclimation method and suspension acclimation method of the present invention, the obtained acclimated cells grow in a stable state, have a good dispersibility, and are suitable for high density, large-scale cultivation, and facilitate the virus replication and expression. When the suspension Vero cells reach a certain cell density before growing to the stationary stage, for example, a cell density of $10.0\times10^6$ cells/mL, the production medium is added to dilute the original culture medium, and then the viruses are inoculated. After the Vero cells are diluted to a low density, they start to grow again, and the viruses also replicate simultaneously, eventually increasing the virus production.

In order to achieve the above production advantages, the present invention firstly provides an acclimation method of making a original adherent Vero cell line capable of high density, suspension growth in a low serum or serum-free medium through changing culture medium and cultivation modes, wherein the term "low serum" means that the serum concentration in the medium is lower than the serum concentration required in the medium when the non-acclimated adherent Vero cell line grows and proliferates normally, for example, low serum means that the serum concentration in the medium is less than 4%, 3%, 2%, 1%, 0.5% or less, preferably, the serum concentration is less than 1.5%, more preferably, the serum concentration is less than 1%. The term "serum-free" means that the medium does not contain any animal-derived serum or ingredients thereof. The concentration is a volume percentage concentration. The low-serum acclimation of the adherent Vero cells comprises gradually reducing the serum concentration of the medium during the passage of the cells until the Vero cells are adapted to the cultivation conditions at a low serum concentration, such as a 1% serum concentration. Then, the adherent Vero cells adapted to the low serum cultivation conditions are subjected to suspension cultivation adaptation under the low serum conditions to obtain suspension Vero cells adapted to the low serum suspension cultivation. The suspension Vero cells can be continuedly adapted to a serum-free, chemically defined growth medium. Specifically, these low serum, suspension, and serum-free acclimations can be performed as follows. The Vero cells in the best state and stably growing are passaged and proliferated in a cell culture medium suitable for Vero cell proliferation and passage containing 5%, 4%, 3%, 2%, 1% animal serum such as newborn bovine serum in turn, such as Celhappy® BD004 (JSB-DP049) complete low-serum culture medium, to make them gradually adapt to a medium containing 1% animal serum. At this time, the adherent Vero cells are in good conditions and can grow normally. Then, the obtained Vero cells are subjected to suspension adaptation in a commercially available, serum-free chemically defined growth medium such as Celkey® CD Vero 211 (JSB-DP211). After several times (for example, 2 to 5 times) of proliferations and passages the cell density can reach $2.0\times10^6$ cells/mL~$4.0\times10^6$ cells/mL, the viability is above 95%, and the dispersibility is good and there are no large cell aggregates, that is, suspension Vero cells which are capable of passaging 100 generations continuously, and can reach a highest density of $8.0\times10^6$ cells/mL to $20.0\times10^6$ cells/mL, which are adapted for the cultivation with a serum-free, chemically defined growth medium. The initial acclimatization usually requires a higher seeding density, such as $0.5\times10^6$ cells/mL~$1.0\times10^6$ cells/mL. If Vero cells grow slowly or stagnate during the initial acclimation, and the viability remains low, a 3 to 5 days passage can be chosen, and centrifugal medium exchange methods can be employed during passaging. If the cell growth is extremely slow during the acclimatization process, the culture volume can be adjusted appropriately, and then medium replacement is performed from time to time.

The initial Vero cells in the best state and stably growing for low serum acclimatization may be Vero cells thawed and recovered from cryopreserved adherent Vero cells. Specifically, the thawing and recovery involve thawing the cryopreserved adherent Vero cells, culturing the thawed cells in a basal medium (such as Celhappy® BD004 (JSB-DP049) complete low serum culture medium) comprising normal concentration of serum such as 5% fetal calf serum or newborn bovine serum, and passaging for 2 to 4 times continuously when the cells reach 90% confluence until the cells recover to the best state and grow stably.

In some embodiments, the low serum acclimation or serum-free acclimation and/or suspension cultivation acclimation comprise the following steps:

(1) thawing the cryopreserved adherent Vero cells, source: ATCC accession No. CCL-81;

(2) transferring the thawed adherent Vero cells in a T75 culture flask, adding 15 mL of Celhappy® BD004 (JSB-DP049) complete low serum culture medium containing 5% newborn bovine serum, maintaining in an incubator at 37° C., 5% $CO_2$, humidity ≥80% for 3 days, to let the cells reach 90% confluence;

(3) discarding the medium and adding 2 mL of 0.25% Trypsin-EDTA to digest and detach the Vero cells off the surface of the flask, then adding 10 mL of Celhappy® BD004 (JSB-DP049) complete low serum culture medium containing 5% newborn bovine serum to terminate the trypsin digestion;

(4) pipetting the above digested cells, calculating the cell density and cell viability per unit volume with a cell counter, reseeding the cells in a T75 culture flask at a seeding density of 14000 cells/cm², adding 15 mL of Celhappy® BD004 (JSB-DP049) complete low serum culture solution containing 5% newborn bovine serum, incubating the cells in an incubator at 37° C., 5% $CO_2$ for 3 days, to let the cells reach to 90% confluence;

(5) passaging the cells every 3 days, reducing the newborn bovine serum concentration in Celhappy® BD004 (JSB-DP049) medium to 5%, 4%, 3%, 2%, 1% step by step, repeating steps (3) and (4) till the cells can still grow normally when the concentration of newborn bovine serum is reduced to 1%, that is, the Vero cells are adapted to Celhappy® BD004 (JSB-DP049) medium plus 1% newborn bovine serum; discarding the culture medium from the last cultured adherent Vero cells and adding 0.25% Trypsin-EDTA to digest and detach the Vero cells off the surface of the flask, then adding 5 mL 10 mL of Celhappy® BD004 (JSB-DP049) medium supplemented with 1% newborn bovine serum to stop the trypsin digestion, centrifuging at 1000 rpm for 5 min, removing the supernatant and collecting the Vero cells;

(6) resuspending the cells with serum-free chemically defined growth medium Celkey® CD Vero211 (JSB-DP211) in a 125 mL suspension culture shake flask, pipetting the cell mass to make the cells disperse, adjusting the cell seeding density to $0.5 \times 10^6$ cells/mL $1.0 \times 10^6$ cells/mL and the culture volume to 30 mL-50 mL, incubating the cells in a shaker at 37° C., 5% $CO_2$, humidity ≥80%, 120 rpm for 3 days; passaging the cells when the cell density is $1.0 \times 10^6$ cells/mL~$2.0 \times 10^6$ cells/mL and the viability is more than 90%;

(7) centrifuging the cell suspension cultivated in the shake flask at 1000 rpm for 5 min, removing the supernatant and collecting the Vero cells, repeating step (6), and passaging the cells every 3 days at the seeding density of $0.3 \times 10^6$ cells/mL~$0.5 \times 10^6$ cells/mL; observing the cell mass and cell dispersion until the cell density reaches $2.0 \times 10^6$ cells/mL to $4.0 \times 10^6$ cells/mL after 3 days of cultivation, with a viability above 95%, and a good dispersibility and no large cell aggregates, that is, the cells can be passaged continuously for 100 generations of which the highest cell density can reach $8.0 \times 10^6$ cells/mL~$20.0 \times 10^6$ cells/mL, and these suspended Vero cells adapt to serum-free chemically defined growth medium Celkey® CD Vero211 (JSB-DP211); cryopreserving the cells at a concentration of $15.0 \times 10^6$ cells/mL in a process cooling box in a refrigerator at −80° C. for 24 h, and then transferring the cryotube to a liquid nitrogen tank for storage.

In addition, in order to achieve the above production advantages, the present invention also provides a second-order (two-stage) culture process for the production of VERO cell-associated vaccines. The specific process and steps are as follows:

1) cell growth: growing the VERO cells in a growth medium such as Celkey® CD VERO211 (JSB-DP211) to a density of $2.0 \times 10^6$ cells/mL to $20.0 \times 10^6$ cells/mL, preferably, $6.0 \times 10^6$ cells/mL~$15.0 \times 10^6$ cells/mL, more preferably, $8.0 \times 10^6$ cells/mL~$12.0 \times 10^6$ cells/mL, most preferably, $10.0 \times 10^6$ cells/mL;

2) inoculation: According to the production process, on day 2 or day 3 of cell growth, when the cell density reaches $6.0 \times 10^6$ cells/mL~$10.0 \times 10^6$ cells/mL, inoculating the cells in an inoculation amount of $10^{-1}$~$10^{-5}$ MOIs, preferably, $10^{-1}$~$10^{-4}$ MOIs, more preferably, $10^{-1}$~$10^{-3}$ MOIs, and most preferably, $10^{-2}$ MOIs; alternatively, inoculating the cells according to the inoculation amount above after dilution;

3) supplementation of medium: supplementing the production medium with the fresh production medium 1 to 5 times the volume of the original growth medium, preferably 1 to 4 times, more preferably 1 to 3 times, most preferably 2 times, to let the cell density reach $1.0 \times 10^6$ cells/mL to $10.0 \times 10^6$ cells/mL, preferably, $1.0 \times 10^6$ cells/mL to $5.0 \times 10^6$ cells/mL, most preferably, $5.0 \times 10^6$ cells/mL;

4) secondary growth: continually growing the cells.

In some embodiments, after the cell density of the secondary growth in step 4) meets the process requirements, steps of harvesting and purifying virus solution for vaccine preparation according to a production process are comprised, wherein the production process refers to a known production process for producing the corresponding vaccines with the Vero cells.

In step 1), the cell growth temperature is 35-37° C., for example, 35° C., 35.5° C., 36° C., 36.5° C., 37° C. The suspension Vero cells are the suspension VERO cells low serum acclimated or serum-free acclimated and/or suspension cultivation acclimated as described above.

In step 2), the inoculation amount is between $10^{-1}$~$10^{-5}$ MOIs, which is controlled by the specific production process and the relationship between the virus and the cell. The virus production temperature is between 30 and 37° C., for example, 30° C., 32° C., 33° C., 34° C., 35° C., 35.5° C., 36° C., 36.5° C., 37° C.

The amount of the supplemented production medium in step 3) is 1 to 5 times of the original growth medium.

The term "growth medium" refers to a low serum or serum-free cell culture medium used for low density growth to high density growth of the cells.

The term "production medium" refers to a virus production medium that can satisfy efficient virus replication.

The "growth medium" and "production medium" of the present invention may be any medium known in the art that can be used for the growth and production of suspension Vero cells.

In some embodiments of the present invention, the "growth medium" and the "production medium" are a same medium, for example, both are commercially available Celkey® CD Vero211 serum-free cell culture medium (JSB-DP211) from Jianshun Bio. In other embodiments of the present invention, the "growth medium" and the "production medium" are different media from each other, for example, the ratio of the "growth medium" to the "production medium" is 1:1, 1:2, 1:3, 1:4, or 1:5.

The present invention relates to the low-serum cultivation and serum-free cultivation of Vero cells. The viruses used for production include all the viruses capable of infecting Vero cells including rabies vaccine (RV), porcine epidemic diarrhea vaccine (PEDV), Japanese encephalitis vaccine, and polio vaccine and the like.

The term "low serum cultivation" refers to a cultivation mode in which 0.1% to 3% bovine serum is added during the cultivation process to satisfy the growth of the cells, for example, 0.5%, 1%, or 1.5% bovine serum.

"Serum-free cultivation" refers to a cultivation mode in which no animal serum such as bovine serum is added during the cultivation process, and the growth of cells are satisfied by the nutrient components provided by the culture medium per se.

The production process is a bioreactor of 30 L and above, including stirred bioreactors and turbulent bioreactors, such as 50 L, 100 L, 200 L, 300 L, 400 L, 500 L, 1000 L, 2000 L, 3000 L, 4000 L, 5000 L, 10000 L or even larger bioreactors.

The term "second-order" (two-stage) culture method refers to a culture method as follows: after growth of 2 to 8 days from the seeding density, the Vero cells can reach a cell density of $2.0 \times 10^6$ cells/mL to $20.0 \times 10^6$ cells/mL, and then the cells are inoculated and adsorb viruses for 0.5~2 h, preferably 0.6~1.5 h, more preferably 0.7~1.2 h, more preferably 0.8~1.1 h, most preferably 1 h, and then production medium 1-5 times of the original working volume is added to reduce the cell density to $1.0 \times 10^6$ cells/mL~$10.0 \times 10^6$ cells/mL. The virus production is carried out for 1-7 days and the virus solution is harvested for vaccine preparation. Of course, the inoculation step can be carried out after supplementing the production medium with 1 to 5 times of the original working volume. This technology is suitable for the production of human vaccines and veterinary vaccines.

The term "seeding density" usually refers to the process of diluting high-density cells to a low density according to a ratio when the cells grow to a high density and the nutritional ingredients of the medium cannot meet the requirement of the growth of the cells, generally the seeding density is 0.1 to $2.0\times10^6$ cells/mL.

The term "stationary stage" in the present invention refers to the time when the cells reach the highest density, and the term "before stationary stage" refers to the time before the cells reach the highest density.

The expression of "the cells reach the highest density" in the present invention refers to the highest growth density that the medium can satisfy the growth of the cells.

Apparently, according to the disclosure of the present invention above and the common knowledge and conventional methods in the art, various forms of modifications and changes can be made without departing from the basic technical idea of the present invention.

The following non-limiting examples will further illustrate the present invention. Those skilled in the art know that many modifications can be made to the present invention without departing from the spirit of the present invention, and such modifications also fall within the scope of the present invention.

Unless otherwise specified, the following experimental methods are conventional methods. The cell line used has the characteristics of the cell line identified as the American Type Culture Collection (ATCC) accession No. CCL-81, which is commercially available. The media used are all products independently developed and marketed by Jianshun Bio. Unless otherwise specified, other experimental materials used can be obtained from commercial companies.

Example 1 Serum-Free Acclimation and Suspension Method of Vero Cells

1. Experimental Materials (1) Cell line: Vero cell line CCL-81 from ATCC;

Culture medium: Celhappy® BD004 (JSB-DP049) complete low serum culture medium, which has been marketed.

2. The Processes

The following steps are comprised:

(1) thawing the cryopreserved adherent Vero cells, source: ATCC accession No. CCL-81;

(2) transferring the thawed adherent Vero cells in a T75 culture flask, adding 15 mL of Celhappy® BD004 (JSB-DP049) complete low serum culture medium containing 5% newborn bovine serum, maintaining in an incubator at 37° C., 5% $CO_2$, humidity ≥80% for 3 days, to let the cells reach 90% confluence;

(3) discarding the medium and adding 2 mL of 0.25% Trypsin-EDTA to digest and detach the Vero cells off the surface of the flask, then adding 10 mL of Celhappy® BD004 (JSB-DP049) complete low serum culture medium containing 5% newborn bovine serum to terminate the trypsin digestion;

(4) pipetting the above digested cells, calculating the cell density and cell viability per unit volume with a cell counter, reseeding the cells in a T75 culture flask at a seeding density of 14000 cells/$cm^2$, adding 15 mL of Celhappy® BD004 (JSB-DP049) complete low serum culture solution containing 5% newborn bovine serum, incubating the cells in an incubator at 37° C., 5% $CO_2$ for 3 days, to let the cells reach to 90% confluence;

(5) passaging the cells every 3 days, reducing the newborn bovine serum concentration in Celhappy® BD004 (JSB-DP049) medium to 5%, 4%, 3%, 2%, 1% step by step, repeating steps (3) and (4) till the cells can still grow normally when the concentration of newborn bovine serum is reduced to 1%, that is, the Vero cells were adapted to Celhappy® BD004 (JSB-DP049) medium plus 1% newborn bovine serum; discarding the culture medium from the last cultured adherent Vero cells and adding 0.25% Trypsin-EDTA to digest and detach the Vero cells off the surface of the flask, then adding 5 mL 10 mL of Celhappy® BD004 (JSB-DP049) medium supplemented with 1% newborn bovine serum to stop the trypsin digestion, centrifuging at 1000 rpm for 5 min, removing the supernatant and collecting the Vero cells;

(6) resuspending the cells with serum-free chemically defined growth medium Celkey® CD Vero211 (JSB-DP211) in a 125 mL suspension culture shake flask, pipetting the cell mass to make the cells disperse, adjusting the cell seeding density to $0.5\times10^6$ cells/mL $1.0\times10^6$ cells/mL and the culture volume to 30 mL-50 mL, incubating the cells in a shaker at 37° C., 5% $CO_2$, humidity ≥80%, 120 rpm for 3 days; passaging the cells when the cell density is $1.0\times10^6$ cells/mL~$2.0\times10^6$ cells/mL and the viability is more than 90%;

(7) centrifuging the cell suspension cultivated in the shake flask at 1000 rpm for 5 min, removing the supernatant and collecting the Vero cells, repeating step (6), and passaging the cells every 3 days at the seeding density of $0.3\times10^6$ cells/mL~$0.5\times10^6$ cells/mL; observing the cell mass and cell dispersion until the cell density reaches $2.0\times10^6$ cells/mL to $4.0\times10^6$ cells/mL after 3 days of cultivation, with a viability above 95% and a good dispersibility and no large cell aggregates, that is, the cells can be passaged continuously for 100 generations of which the highest cell density can reach $15.0\times10^6$ cells/mL.

Example 2 Second-Order Culture Process Test of Porcine Epidemic Diarrhea Virus in Suspension Vero Cells 1. Experimental Materials (1) cell line: Vero cell line CCL-81 derived from ATCC, as described above, which can grow in suspension by independently acclimated by Jianshun Bio.;

Culture medium: Celkey® CD Vero211 serum-free medium (JSB-DP211), which has been marketed.

Virus: PEDV (Hua Nong (Zhaoqing) Biotechnology Research Institute)

2. The Processes

The following steps are comprised.

(1) thawing and passaging the cells

Preparation of a culture medium: preparing liquid medium Celkey® CD Vero 211 20 L according to the instructions, sterilizing by filtration and keeping in dark at 4° C.

(2) thawing the cells: taking out the cryopreserved cell strain from the liquid nitrogen tank, thawing at 37° C., adding to 30 mL medium, centrifuging at 1000 rpm and discarding the supernatant, resuspending the cells in fresh 1×Celkey® CD Vero211 cell culture, incubating in an incubator at 37° C., 5% $CO_2$.

(3) passaging the cells: passaging the newly thawed cells every 3 days for 3 to 4 times before the experiment with an inoculation density of $1\times10^6$ cells/mL, and the passage continued for 3 days, and then carrying out the experiment.
(4) inoculation: inoculating the cells with porcine epidemic diarrhea virus in an inoculation amount of $10^{-2}$ MOIs when the cell density reached $8.0\times10^6$ cells/mL after the cells were passaged to day 3 of the 4th generation. After 1 hour of absorption, supplementing the culture medium to make the cell density to $4.0\times10^6$ cells/mL and then continuing the cultivation, and the cells began to grow again. After 4 days, the cell density reached to $10\times10^6$ cells/mL.
(5) testing the viruses: testing the virus's $TCID_{50}$ according to 50% tissue (cell) culture infective dose.

Experimental Results

Figure 2:
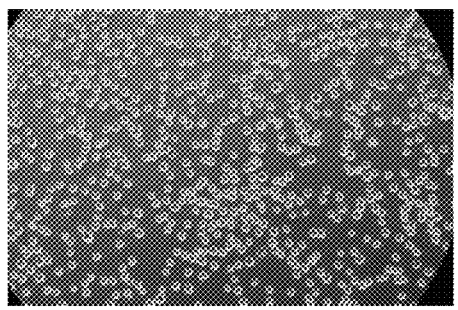
FIG. 2 shows the growth pictures of suspension Vero cells observed under an inverted microscope and the lesion pictures after infection with PEDV virus.
Figure 2:
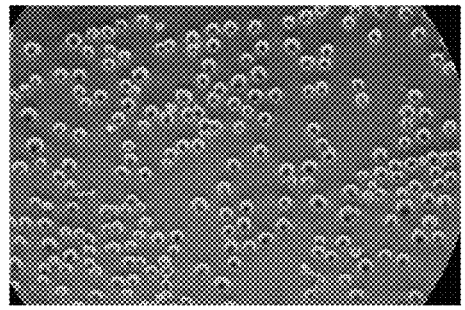
Figure 2:
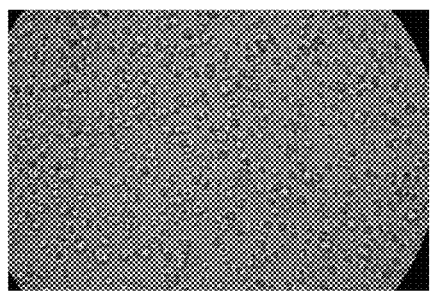
Figure 2:

The results are shown in FIGS. 1 and 2. The virus titer $TCID_{50}$ of porcine epidemic diarrhea virus produced by the second-order culture technology of suspension Vero cell production is $\log_{10} 7.2/0.1$ mL, and the virus yield is 1 titer higher than that of the conventional method (the virus titer $TCID_5O$ obtained by the conventional method is generally $\log_{10}$ 6.0/0.1 mL). The innovation of present invention is that: suspension Vero cells grow in high density ($8.0\times10^6$ cells/mL) on day 3 in Celkey® CD Vero211 serum-free medium, and the cells are infected with porcine epidemic diarrhea virus at a low density ($4.0\times10^6$ cells/mL) after double dilution. After inoculation, the cells of the present invention start to grow again, saving the production cost and increasing the virus titer.

What claimed is:

1. A second-order cultivation method for producing vaccines with suspension Vero cells, comprising the following steps:

1) cell growth: suspension Vero cells are grown in a growth medium to $2.0\times10^6$ cells/mL~$20.0\times10^6$ cells/mL;
2) inoculation: the inoculation amount is between $10^{-1}$~$10^{-5}$ MOIs, or viruses are inoculated after step 3) according to this inoculation amount;
3) dilution/supplementation of a production medium: Diluting 1 to 5 times with the production medium, and after dilution, the cell density reaches $1.0\times10^6$ cells/mL to $10.0\times10^6$ cells/mL;
4) secondary growth: secondary growth of cells;
5) optionally, the virus solution is harvested and purified for vaccine preparation.

2. The second-order cultivation method for producing vaccines with suspension Vero cells according to claim 1, wherein the growth of suspension Vero cells is a suspension cultivation tank cultivation with a cultivation working volume of 30 L and above.

3. The second-order cultivation method for producing vaccines with suspension Vero cells according to claim 1, wherein the cell density in step 1) is $5.0\times10^6$ cells/mL to $16.0\times10^6$ cells/mL.

4. The second-order cultivation method for producing vaccines with suspension Vero cells according to claim 1, wherein the inoculation amount to the cells in step 2) is between $10^{-1}$~$10^{-4}$ MOIs.

5. The second-order cultivation method for producing vaccines with suspension Vero cells according to claim 1, wherein the production medium for suspension Vero cells in step 3) is diluted 1 to 4 times.

6. The second-order cultivation method for producing vaccines with suspension Vero cells according to claim 1, wherein the cell density after inoculation in step 3) is $1.0\times10^6$ cells/mL~$10.0\times10^6$ cells/mL.

7. The second-order cultivation method for producing vaccines with suspension Vero cells according to claim 1, wherein the virus is a virus selected from the group consisting of rabies vaccine (RV), porcine epidemic diarrhea vaccine (PEDV), Japanese encephalitis virus vaccine, and Polio vaccine.

8. The second-order cultivation method for producing vaccines with suspension Vero cells according to claim 1, wherein the cell growth temperature is between 35° C. and 37° C., and the virus production temperature after inoculation is between 30° C. and 37° C.

9. The second-order cultivation method for producing vaccines with suspension Vero cells according to claim 1, wherein the cell growth seeding density is between $0.3\times10^6$ cells/mL to $1.0\times10^6$ cells/mL, and the growth reaches the highest cell density within 2 to 8 days.

10. A second-order cultivation method for producing vaccines with suspension Vero cells, comprising the following steps:

1) cell growth: suspension Vero cells are grown in a growth medium to $2.0\times10^6$ cells/mL~$20.0\times10^6$ cells/mL;
2) inoculation: the inoculation amount is between $10^{-1}$~$10^{-5}$ MOIs, or viruses are inoculated after step 3) according to this inoculation amount;
3) dilution/supplementation of a production medium: Diluting 1 to 5 times with the production medium, and after dilution, the cell density reaches $1.0\times10^6$ cells/mL to $10.0\times10^6$ cells/mL;
4) secondary growth: secondary growth of cells;
6) optionally, the virus solution is harvested and purified for vaccine preparation, wherein the suspension Vero cells are suspension cells used for vaccine production, or suspension Vero cells acclimated from adherent Vero cells and capable of suspension growth and production which are obtained from adherent Vero cells by low serum acclimation or serum-free acclimation and by suspension acclimation, wherein "serum-free acclimation" means that the acclimated Vero cells can grow and proliferate in a medium without serum.

11. The second-order cultivation method for producing vaccines with suspension Vero cells according to claim 10, wherein the suspension acclimation of adherent Vero cells comprises the following steps:

1) adapting the adherent cells to low serum cultivation;
2) suspension cultivation of the adherent cells adapted to low serum with a total suspension medium.

12. The second-order cultivation method for producing vaccines with suspension Vero cells according to claim 11, wherein the adherent Vero cell is the adherent Vero cell designated as ATCC accession No. CCL-81.

13. The second-order cultivation method for producing vaccines with suspension Vero cells according to claim 11, wherein the cultivation adapted low serum of the adherent cells comprises the following low serum adaption steps: a) optionally, thawing the adherent Vero cells, b) resuspending the cells with a low serum medium plus 5% newborn bovine serum and incubating; c) collecting the cells and reseeding them in a flask, adding reduced concentration of serum of 4%, 3%, or 2% newborn bovine serum, incubating the cells in an incubator at 37° C., 5% $CO_2$; d) passaging the cells and reducing the serum in the low serum medium to 3%, 2%, 1% step by step till the cells can grow normally when the serum concentration is reduced to 1%.

14. The second-order cultivation method for producing vaccines with suspension Vero cells according to claim 11, wherein suspension cultivation of the adherent cells adapted to low serum with a total suspension medium comprises the following steps: i) resuspending the adherent cells adapted to low serum with a serum-free chemically defined growth medium in a suspension culture shake flask, pipetting the cell aggregates to make the cells disperse, adjusting the cell seeding density to $0.5~1.0\times10^6$ cells/mL; ii) growing the cells to a cell density of $1.0~2.0\times10^6$ cells/mL and a viability above 95%, and then passaging the cells; iii) centrifuging the culture of step ii) to collect the cells, repeating steps i)~ii) until the cell density reaches $2.0\times10^6$ cells/mL to $4.0\times10^6$ cells/mL after 3 days of cultivation, with a viability above 95%, and a good dispersibility and no large cell aggregates and the highest cell density even reaches $8.0\times10^6$ cells/mL to $20.0\times10^6$ cells/mL; iv) optionally, centrifuging and collecting the final culture obtained in step iii) and cryopreserving the cells at a concentration of $15.0\times10^6$ cells/mL in a process cooling box in a refrigerator at −80° C. for 24 h, and then transferring the cryotube to a liquid nitrogen tank for storage.

\* \* \* \* \*